US008101781B2

(12) United States Patent
Kim et al.

(10) Patent No.: US 8,101,781 B2
(45) Date of Patent: Jan. 24, 2012

(54) PROCESS FOR THE PREPARATION OF HIGHLY OPTICAL PURE CARVEDILOL

(75) Inventors: Seong-Jin Kim, Daejeon (KR); Chang Woo Jong, Jeollabuk-do (KR); Hyun Bin Kang, Incheon (KR); Byung Hyun Moon, Incheon (KR); Long Guo Quan, Daejeon (KR); Duk Kwon Won, Gyeonggi-do (KR); Kyung Yong Jin, Seoul (KR)

(73) Assignees: AHN-Gook Pharmaceutical Co., Ltd., Seoul (KR); RSTech Corporation, Daejeon (KR)

( * ) Notice: Subject to any disclaimer, the term of this patent is extended or adjusted under 35 U.S.C. 154(b) by 456 days.

(21) Appl. No.: 12/280,684

(22) PCT Filed: Aug. 31, 2006

(86) PCT No.: PCT/KR2006/003439
§ 371 (c)(1),
(2), (4) Date: Dec. 22, 2008

(87) PCT Pub. No.: WO2007/097504
PCT Pub. Date: Aug. 30, 2007

(65) Prior Publication Data
US 2009/0176992 A1 Jul. 9, 2009

(30) Foreign Application Priority Data

Feb. 23, 2006 (KR) .......................... 10-2006-0017781

(51) Int. Cl.
*A61K 31/403* (2006.01)
*C07D 209/88* (2006.01)

(52) U.S. Cl. .......................... 548/440; 548/444; 514/411

(58) Field of Classification Search .......................... None
See application file for complete search history.

(56) References Cited

FOREIGN PATENT DOCUMENTS

| EP | 0918055 A1 | 5/1999 |
| EP | 1142874 A2 | 10/2001 |
| KR | 10-2005-0003764 A | 1/2005 |
| KR | 100746455 B1 | 7/2007 |
| WO | 01-87837 A1 | 11/2001 |
| WO | W001/87837 A1 | 11/2001 |
| WO | 02-00216 A1 | 1/2002 |
| WO | 2004/041783 A1 | 5/2004 |
| WO | 2004/113296 A1 | 12/2004 |
| WO | 2005/080329 A2 | 9/2005 |
| WO | 2005/113502 A1 | 12/2005 |
| WO | 2005/115981 A2 | 12/2005 |
| WO | 2006/061364 A1 | 6/2006 |

OTHER PUBLICATIONS

International Preliminary Report on Patentability dated Aug. 26, 2008 for International Patent Application PCT/KR2006/003439.
Office Action for Russian Application No. 2008137790, (2008).
Russian article, vol. 1, p. 489, col. 953, p. 55, col. 102, pp. 97-98, cols. 186-187, vol. 4, p. 607, col. 1205.
Office Action for Russian Application No. 200813790, (2008).

*Primary Examiner* — Yong Chu
*Assistant Examiner* — Michael Barker
(74) *Attorney, Agent, or Firm* — LRK Patent Law Firm

(57) ABSTRACT

The present invention relates to a process for the efficient preparation of highly optical pure chiral carvedilol. According to the present invention, a chiral oxazolidin-2-one or oxazolidin-2-thione having formula 2, produced from the reaction of N-protected 2-(2-methoxyphenoxy)ethylamine with a chiral glycidol derivative is used as a key intermediate for the preparation of the chiral carvedilol. Specifically, the process for the preparation of the chiral carvedilol comprises a) reacting a compound of formula 2 with a halogenation agent, a sulfonation agent or a mitsunobu reagent to activate a hydroxyl group of the compound of formula 2, followed by nucleophilic substitution reaction with 9H-4-hydroxy carbazole to produce a compound of formula 7, and b) subjecting the obtained compound of formula 7 to a deprotection reaction in a presence of an inorganic base to produce the targeted chiral carvedilol. The process of the present invention can be accomplished in a mild condition. The process neither requires any extraordinary purification procedure, nor involves decrease of optical purity. Therefore, the process of the present invention provides highly optical pure chiral carvedilol in simple and efficient manner.

13 Claims, No Drawings

PROCESS FOR THE PREPARATION OF HIGHLY OPTICAL PURE CARVEDILOL

TECHNICAL FIELD OF THE INVENTION

The present invention relates to a process for the preparation of carvedilol. More specifically, the present invention relates to a process for the efficient preparation of chiral carvedilol.

BACKGROUND OF THE INVENTION

Most of medicines that have been recently developed and commercially available are chiral products. This is attributed to side effects or decreased efficacies caused by racemic drugs. Therefore, in order to increase both the safety and the efficacy, studies to develop chiral drugs containing optically pure stereoisomers has been widely attempted. In the chiral drugs, high chemical purity and high optical purity are required for ensuring the safety and the efficacy.

Carvedilol (IUPAC NAME: 1-(9H-carbazol-4-yloxy)-3-[[2-(2-methoxyphenoxy)ethyl]amino]-2-propanol) is a compound having formula 1:

Formula 1

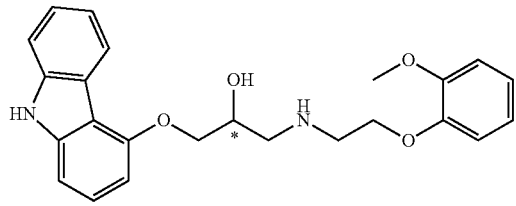

wherein, * represents a chiral center.

As shown in the formula 1, the carvedilol has one chiral center, and may exist in either (R)-isomer or (S)-isomer. Herein, as a blocker of $\alpha_1$-adrenoreceptor, (R)-isomer and (S)-isomer exhibit almost the same activities. To the contrary, as a blocker of $\beta_1$-adrenoreceptor, (S)-isomer has an enhanced, superior activity to (R)-isomer [EP 127,099; Chirality 1989, 1, 265; J. Pharm. Exp. Ther., 1992, 263, 92; Clin. Pharmacokin., 1994, 26, 335; Cardiovasc. Res., 1994, 28, 400; J. of Chromatography B. 1996, 682, 349]. Further, the carvedilol is now used as an antioxidant, anti-inflammatory agent, anti-apoptotic agent [The American Journal of Cardiology, 2004, 93(9A), 3B]. For these reasons, provision of a process for the efficient preparation of highly optical pure chiral carvedilol in an economic manner is an important task to the development of various drugs comprising the chiral carvedilol.

Conventional processes for the preparation of the chiral carvedilol are shown in a reaction scheme 1:

Reaction Scheme 1

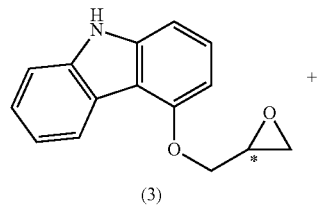

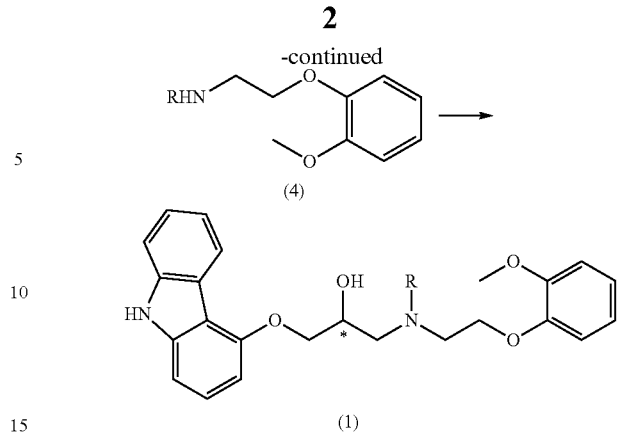

wherein, R represents hydrogen or a benzyl group.

As shown in the reaction scheme 1, the targeted carvedilol was prepared from ring opening of a chiral epoxy-carbazole of formula 3 with an ethylamine compound of formula 4 [R=hydrogen, U.S. Pat. Nos. 4,503,067 and 4,697,022]. However, the process leads to formation of a bis-substituted side product that is not easy to be removable in the purification procedure. The process requires an extraordinary purification procedure, thereby hindering the preparation of highly optical pure carvedilol. Furthermore, loss of the targeted carvedilol is inevitable in the purification procedure, which results in significant decrease of the yield of the carvedilol.

In order to avoid the disadvantage resulted from the bis-substituted side product, other attempts have been performed. In order to prevent the formation of the bis-substituted side product, a N-protected compound of formula 4 (R=benzyl) was used as a starting material in the reaction scheme 1 and applied to ring opening of a chiral epoxy compound of formula 3 [R=benzyl, EP 918,055]. The process produces no bis-substituted side product. However, it suffered from the disadvantage that an expensive palladium catalyst should be used in order to deprotect the benzyl group.

As an alternative, the ethylamine compound of formula 4 was used in an excess over the compound of formula 3 to reduce the formation of the bis-substituted side product [R=hydrogen, WO 02/00216]. Even though the process could reduce the formation of the bis-substituted side product, there still remain problems caused from small amount of the bis-substituted side product. In addition, the process suffered from low price competitiveness due to excess use of the expensive ethylamine compound.

In addition, the ethylamine compound of formula 4 or its benzylated form undergoes degradation by exposure to air and light. Therefore, the compound of formula 4 has a limitation to the application to mass production. In order to overcome the disadvantage, acid addictive salt of the ethylamine compound of formula 4 (R=H) was used as a starting material in the ring opening reaction with the compound of formula 3 to increase the stability [WO 2004/041783]. The process has an advantage applicable to mass production of the chiral carvedilol. Nonetheless, it suffered from the formation of the bis-substituted side product and from excess use of the ethylamine compound.

In order to avoid the formation of the bis-substituted side product, new attempt has been tried.

The amine group of the compound of formula 4 was firstly protected with a benzyl group, and a chloro-propaiionyl group was introduced thereto. The obtained product was alkylated with a 9H-4 hydroxy carbazole of formula 8, followed by a reduction step and a debenzylation step to produce the carvedilol (Korean Published Patent No. 2005-0003764). However, the process requires a strong reducing agent such as sodium borohydride or lithium borohydride and an expensive palladium catalyst.

Further another process for the preparation of the carvedilol known in the art comprises reacting the amine compound of formula 4 with a carbonated compound to produce a carbamate having two leaving groups, followed by cyclization reaction to produce a oxazolidinone compound that is used as an intermediate for the synthesis of the carvedilol [EP 1,282,601 and 1,367,052]. In the process, the oxazolidinone compound was alkylated with 9H-4-hydroxy carbazole and deprotected to produce the carvedilol.

Even though the above two processes effectively inhibits the formation of the bis-substituted side product, they are not suitable for the production of chiral carvedilol.

As mentioned in the above, the conventional methods had one or more unresolved technical problems for the application to mass production of highly optical pure chiral carvedilol. Therefore, an efficient process for the preparation of highly optical pure chiral carvedilol is now urgently demanded.

SUMMARY OF THE INVENTION

According to our inventors' extensive studies, it was found that efficient preparation of highly optical pure key intermediate and provision of efficient chemical synthesis routes are crucial to efficient mass production of the chiral carvedilol.

As a result of our inventors' profound studies, there is provided a process for the preparation of chiral carvedilol, wherein a chiral oxazolidinone having formula 2 is used as a key intermediate. The key intermediate of formula 2 can be effectively synthesized by reacting highly optical pure chiral glycidol derivative with N-protected 2-(2-methoxyphenoxy) ethylamine, both of which are commercially available and industrially mass produced.

Formula 2

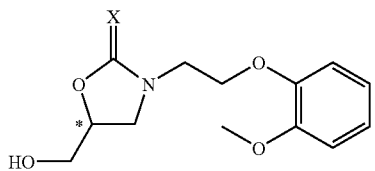

wherein, * represent a chiral center and X represents oxygen or sulfur.

The preparation of the chiral carvedilol from the key intermediate of formula 2 comprises a) reacting a compound of formula 2 with a halogenation agent, a sulfonation agent or a mitsunobu reagent to activate a hydroxyl group of the compound of formula 2, followed by nucleophilic substitution reaction with 9H-4-hydroxy carbazole to produce a compound of formula 7, and b) subjecting the obtained compound of formula 7 to a deprotection reaction in a presence of an inorganic base to produce the targeted chiral carvedilol.

Specifically, the compound of formula 2 is prepared from a ring opening reaction and subsequent in-situ intramolecular cyclization reaction between an amine compound of formula 4 and a chiral glycidol of formula 5, followed by deprotection reaction, and then, the chiral carvedilol with a highly optical purity is produced from the compound of formula 2. Herein, the amine compound of formula 4 effectively prohibits the formation of the bis-substituted side product and produces an oxazolidin-2-one or oxazolidin-2-thione of formula 2 through a ring opening reaction with the compound of formula 5 and subsequent in-situ intramolecular cyclization reaction. Thereafter, the hydroxyl group of the compound of formula 2 thus obtained is activated with aid of a halogenation agent, a sulfonation agent or a mitsunobu reagent, and undergoes nucleophilic substitution reaction with 9H-4-hydroxy carbazole to produce the compound of formula 7 (5-(9H-carbazol-4-yloxymethyl)-3-[2-(2-methoxy-phenoxy)-ethyl]-oxazolidin-2-one or (5-(9H-carbazol-4-yloxymethyl)-3-[2-(2-methoxy-phenoxy)-ethyl]oxazolidin-2-thione). The compound of formula 7 is ring-opened in a presence of an inorganic base to produce the chiral carvedilol of formula 1.

The process of the present invention is safe and industrially applicable, and it provides the chiral carvedilol in a highly optical pure form.

DETAILED DESCRIPTION OF THE INVENTION

The present invention relates to a process for the efficient preparation of chiral carvedilol, comprising a) reacting a compound of formula 2 with a halogenation agent, a sulfonation agent or a mitsunobu reagent to activate a hydroxyl group of the compound of formula 2, followed by nucleophilic substitution reaction with 9H-4-hydroxy carbazole to produce a compound of formula 7, and b) subjecting the obtained compound of formula 7 to a deprotection reaction in a presence of an inorganic base to produce the targeted chiral carvedilol. The process is summarized in a reaction scheme 2:

Reaction Scheme 2

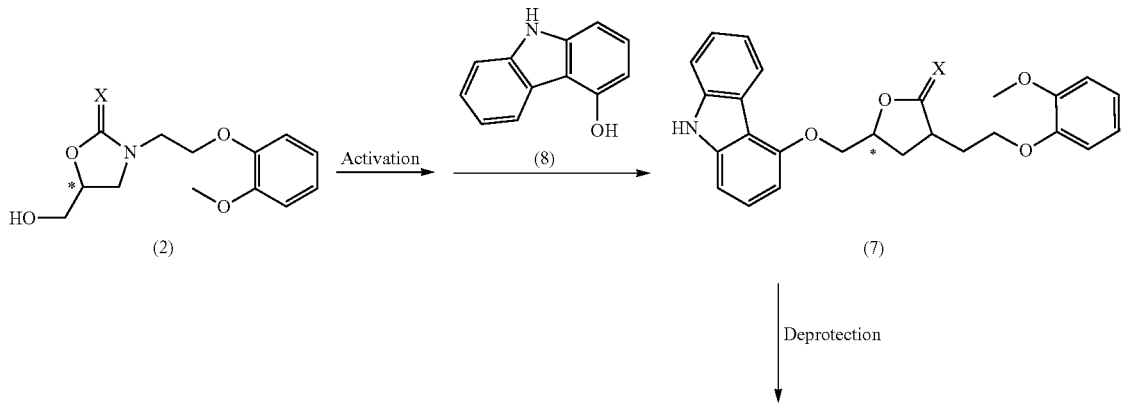

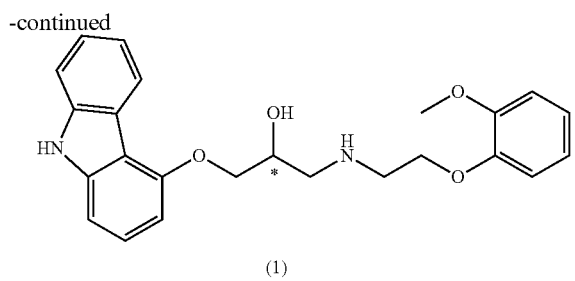

(1)

In the reaction scheme 2, * represents a chiral center and X represents oxygen or sulfur.

As shown in the reaction scheme 2, the present invention uses, as a chiral key intermediate, chiral oxazolidin-2-one or oxazolidin-2-thione having formula 2 of which the nitrogen atom is substituted with 2-(2-methoxy-phenoxy)ethyl group.

The key intermediate is prepared from ring opening of a chiral glycidol compound of formula 5 by an amine compound of formula 4 and subsequent in-situ intramolecular cyclization, followed by a hydroxy deprotection of a compound of formula 6.

Specific example of the amine compound of formula 4 used in the preparation of the chiral key intermediate of formula 2 is as follows:

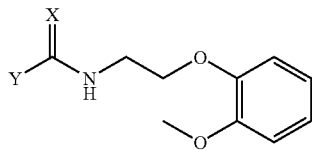

Formula 4 wherein, X represents oxygen or sulfur, and Y represent a leaving group.

The compound of formula 4 can be produced in known procedure using a corresponding primary amine compound. Particularly, when X is an oxygen atom, it can be produced by reacting the primary amine compound with a carboxylic acid, a carboxylic acid ester, a carbonyl halide compound, a carboxylic acid anhydride or halo formate.

When X is a sulfur atom, the compound of formula 4 can be produced by reacting the primary amine compound with a thiocarboxylic acid ester [*J. Chem. Soc. C.,* 1969, 2631; *Chem. Ber.* 1971, 104, 3146], or its corresponding isothiocyanate [*Chem. Ber.* 1914, 47, 1255; *J. Am. Chem. Soc.,* 1968, 90, 6008; *J. Chem. Eng. Data,* 1980, 25, 176]. Preferable examples of the leaving group Y are $C_1$~$C_{10}$ alkoxy group, $C_6$~$C_{10}$ aryloxy group, allyloxy group, $C_7$~$C_{14}$ alkylaryloxy group.

Specific example of the chiral glycidol compound of formula 5 used in the preparation of the chiral key intermediate of formula 2 is as follows:

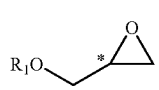

Formula 5

In the formula 5, * represents a chiral center and $R_1$ represents a hydroxy protecting group. Preferable examples of $R_1$ include $C_1$~$C_{10}$ alkyl group, $C_2$~$C_{10}$ alkenyl group, $C_2$~$C_{10}$ alkynyl group, $C_1$~$C_{10}$ alkoxy group, ($C_1$~$C_{10}$)-alkyloxycarbonyl group, $C_6$~$C_{10}$ aryl group, $C_3$~$C_{10}$ cycloalkyl group, $C_4$~$C_{10}$ cycloalkenyl group, heterocycle or polycycle group, $C_2$~$C_{10}$ carbonyl group, $C_2$~$C_{10}$ carboxyl group, silyl group, ether group, thioether group, selenoether group, ketone group, aldehyde group, ester group, phosphoryl group, phosphonate group, phosphine group, sulphonyl group or —$(CH_2)_k$—$R_2$ (wherein, $R_2$ represents $C_2$~$C_{10}$ alkenyl group, $C_2$~$C_{10}$ alkynyl group, $C_1$~$C_{10}$ alkoxy group, ($C_1$~$C_{10}$)-alkyloxycarbonyl group, $C_6$~$C_{10}$ aryl group, $C_3$~$C_{10}$ cycloalkyl group, $C_4$~$C_{10}$ cycloalkenyl group, heterocycle or polycycle group, $C_2$~$C_{10}$ carbonyl group, $C_2$~$C_{10}$ carboxyl group, silyl group, ether group, thioether group, selenoether group, ketone group, aldehyde group, ester group, phosphoryl group, phosphonate group, phosphine group, sulphonyl group and k is an integer of 1 to 8).

The chiral glycidol of formula 5 is commercially available and can be easily produced from a known procedure. Specifically, the chiral glycidol can be prepared from asymmetric epoxidation reaction of an allylalcohol [U.S. Pat. Nos. 4,946, 974, 5,153,338 and 5,344,947], from chiral 3-chloro-propandiol [JP 7-165743, U.S. Pat. Nos. 5,965,753 and 2,248,635, and DE 1,226,554], or from asymmetric catalytic reaction using enzyme or metallic catalyst [*J. Am. Chem. Soc.* 1984, 106, 7250; *Tetrahedron Asymmetry* 1991, 2, 481; *Enzyme Microb. Technol* 1991, 13, 306; *Biotech. Tech,* 1998, 12, 225; *Tetrahedron* 1994, 40, 8885; *Biotech. Bioeng,* 1996, 49, 70; *Acta Chem, Scand.* 1996, 50, 249; *Tetrahedron Asymmetry* 1997, 8, 639; *Biotech. Tech,* 1998, 12, 225; U.S. Pat. No. 6,720,434; WO 01/89690; JP 2003-534117; EP 289,655; US 2004-0054201; JP 2004-515356; WO 02/48162, KR 2002-01219; U.S. Pat. No. 6,262,278; U.S. Pat. No. 6,448,414; U.S. Pat. No. 6,693,236; U.S. Pat. No. 6,800,766; and WO 00/09463].

Preparation of the chiral oxazolidin-2-one or oxazolidin-2-thione of formula 2, the key intermediate for the synthesis of the chiral carvedilol, from the compound of formula 4 and the compound of formula 5 is summarized in a reaction scheme 3:

Reaction Scheme 3

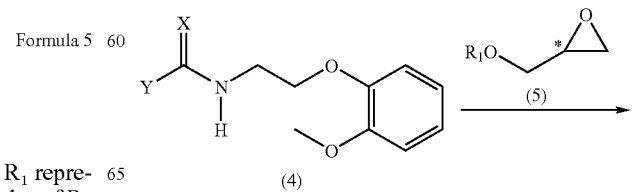

(4) (5)

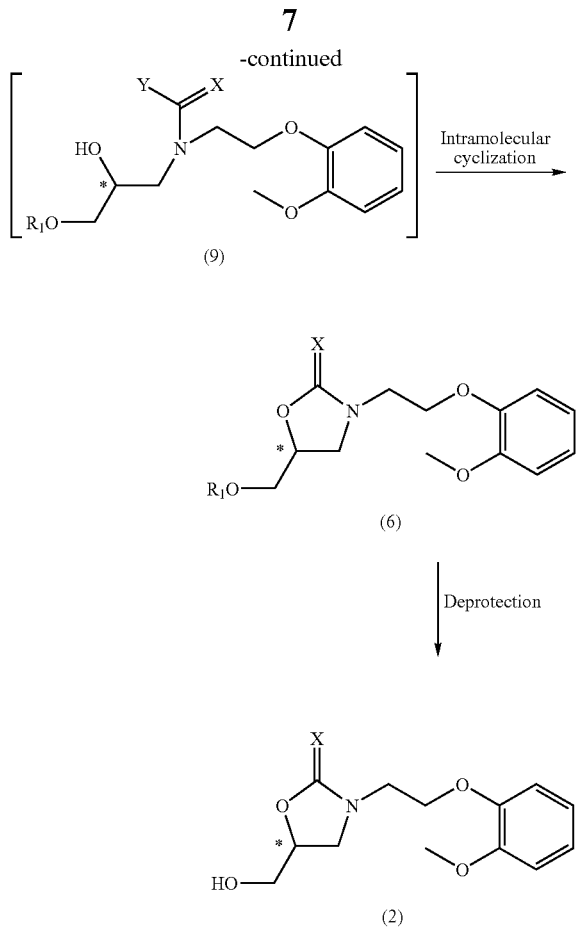

In the reaction scheme 3, * represents a chiral center, and X, Y and $R_1$ is the same as defined in the above.

As shown in the reaction scheme 3, N-protected compound of formula 4 participates in the ring opening of the chiral glycidol of formula 5. As a result thereof, an intermediate represented as formula 9 is produced. The intermediate thus produced undergoes in-situ intramolecular cyclization reaction, thereby producing hydroxy-protected chiral oxazolidin-2-one or oxazolidin-2-thione compound of formula 6.

Herein, the compound of formula 5 is added, based on the compound of formula 4, in an amount of 0.8~5 equivalents, preferable 1~1.5 equivalents. The ring opening reaction and subsequent in-situ intramolecular cyclization reaction are carried out in a presence of a base. The base to be used includes inorganic or organic base. For example, an alkali metal salt such as sodium methoxide, lithium methoxide, sodium carbonate, sodium bicarbonate, potassium carbonate, sodium hydroxide or potassium hydroxide, an imidazole, 2-6-lutidine, N,N-dimethylamino pyridine and salts thereof, tertiary amine and its hydrate form can be used as a base. Organic solvent to be used is not particularly limited. N,N-dimethylformamide, an aliphatic or aromatic hydrocarbon solvent, a halogenated hydrocarbon, and an ether can be used as an organic solvent. Specifically, an aromatic organic solvent such as toluene or benzene, a haloalkane such as dichloromethane or chloroform, or an ether such as ethyl ether, tetrahydrofuran or dioxane can be used. The reaction temperature is preferably adjusted to a range of 0~150° C., more preferably 80~100° C.

The compound of formula 6 thus obtained is applied to the next deprotection reaction without any extraordinary purification (for example, fractional distillation or recrystallization). Specifically, after the completion of consumption of the starting materials and intermediates involved in the ring opening reaction and subsequent in-situ intramolecular cyclization reaction, a deprotecting agent dependent upon the hydroxy protecting group is added to the same reactor to produce the chiral key intermediate of formula 2 [*Protecting Groups*, Thieme Medical Publishers Inc, New York, 1994; *Protective Groups in Organic Synthesis*, John Wiley and Sons, Inc, 1991].

The compound of formula 2 can be also directly applied, without any purification, to an alkylation reaction with the compound of formula 8. In order words, the hetero-ring compound of formula 2 having a hydroxy group is prepared in a highly pure form such that it can be directly applied, as a starting material, to the alkylation and subsequent deprotection steps for the synthesis of the targeted carvedilol.

Preparation of a precursor compound having formula 7 from the compound of formula 2 is accomplished by reacting a compound having formula 2 with a halogenation agent, a sulfonation agent or a mitsunobu reagent to activate a hydroxyl group of the compound having formula 2, followed by nucleophilic substitution reaction with 9H-4-hydroxy carbazole. This is summarized in a reaction scheme 4, wherein activation by the halogenation agent or the sulfonation agent is expressed as pathway (1) and activation by ; the mitsunobu reagent as pathway (2):

Reaction Scheme 4

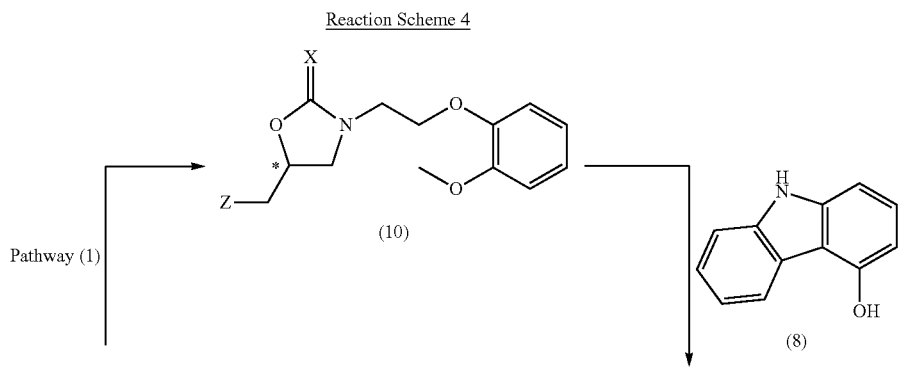

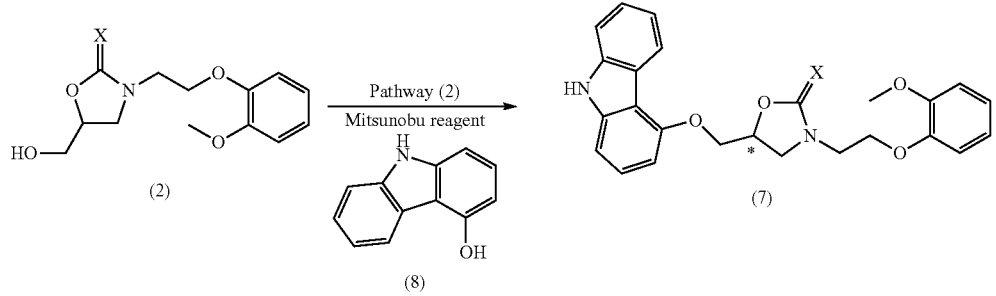

In the reaction scheme 4, * represents a chiral center and Z represents a halogen group or a sulfonate group, and X, Y and R₁ is the same as defined in the above.

As shown in the above, the compound of formula 7 can be prepared by subjecting the compound of formula 2 to halogenation or sulfonation reaction to produce a compound of formula 10, followed by nucleophilic attack by 9H-4-hydroxy carbazole. Alternatively, it can be prepared by mitsunobu reaction of the compound of formula 2 with 9H-4-hydroxy carbazole.

More specifically, as shown in the pathway (1) of the reaction scheme 4, the compound of formula 2 produces a compound of formula 10 by the reaction with a halogenation agent. Herein, examples of the halogenation agent include thionyl chloride, thionyl bromide, oxalyl chloride, phosphorous tribromide and phosphorous trichloride. The halogenation agent is added typically in an amount of 0.8~10 equivalents, preferably 1.1~2.0 equivalents.

Further, the compound of formula 10 can be also prepared from the reaction of the compound of formula 2 with a sulfonation agent (sulfonyl halide) by converting the hydroxy group of the compound 2 to the corresponding a sulfonate group. Herein, examples of the sulfonation agent include methanesulfonyl chloride (shortly, MsCl), p-toluenesulfonyl chloride (shortly, TsCl), benzenesulfonyl chloride, trifluoromethanesulfonyl chloride (shortly, TfCl) and nitrobenzenesulfonyl chloride. The sulfonation agent is added typically in an amount of 0.8~5 equivalents, preferably 1.1~2.0 equivalents.

The halogenation or sulfonation reaction is carried out in a presence of an organic base. As an example of the organic base, an imidazole, 2-6-lutidine, N,N-dimethylamino pyridine and salts thereof, or tertiary amine and its hydrate form can be mentioned. Preferable is a trialkylamine including trimethylamine, triethylamine and diisopropylethylamine. The base is added in an amount of 0.8~10 equivalents, preferably 1.0~3.0 equivalents. The reaction is carried out in a presence of organic solvent. Sometimes, it can be carried out without any solvent. The organic solvent to be used is not particularly limited. N,N-dimethylformamide, an aliphatic or aromatic hydrocarbon solvent, a halogenated hydrocarbon, and an ether can be used as an organic solvent. Specifically, an aromatic organic solvent such as toluene or benzene, a haloalkane such as dichloromethane or chloroform, or an ether such as ethyl ether, tetrahydrofuran or dioxane can be used. The reaction temperature is preferably adjusted to a range of 0~100° C., more preferably 0~20° C.

In the reaction, the compound of formula 10 is produced in a highly pure form through typical work-up procedure. The obtained compound can be directly subjected to the subsequent alkylation reaction, without any extraordinary purification. This simplifies the preparation of the chiral carvedilol and increases the yield of the reaction.

The compound of formula 10 provides a compound of formula 7, which is a precursor of the carvedilol, through the reaction with 9H-4-hydroxy carbazole of formula 8. The 9H-4-hydroxy carbazole of formula 8 is commercially available or can be mass produced through a well-known procedure [DE 2,240,599 and U.S. Pat. No. 4,273,711].

The specific reaction condition between the compound of formula 10 and 9H-4-hydroxy carbazole of formula 8 is as follows. 9H-4-hydroxy carbazole of formula 8 is added, based on the compound of formula 10, in a range of 0.5~2.0 equivalents, preferably, 1.0~1.1 equivalents. First, the compound of formula 10 and 9H-4-hydroxy carbazole of formula 8 are dissolved into an organic solvent. To the solution, 0.1~10 equivalents of a base (preferably, 0.5~2.0 equivalents) is added. Reaction temperature is adjusted to 30~150° C., preferably 70~100° C. The base to be used includes inorganic or organic base. As an example of the inorganic base, sodium carbonate, sodium bicarbonate, potassium carbonate, sodium hydroxide, potassium hydroxide or a metal alkoxide can be mentioned. Preferable is potassium carbonate or sodium carbonate. For the organic base, a trialkylamine compound, for example, trimethylamine, triethylamine or diisopropylethylamine is preferable. Organic solvent to be used is not particularly limited. N,N-dimethylformamide, dimethylsulfoxide, an aliphatic or aromatic hydrocarbon solvent, a halogenated hydrocarbon, an ether or an alcohol can be used as an organic solvent. Preferable example of the alcohol is $C_1$~$C_4$ alcohol such as methanol, ethanol, propanol, isopropanol, butanol, isobutanol or t-butanol.

The obtained compound can be directly subjected to one-pot deprotection reaction, without any extraordinary purification. This attributes to the facts that the procedure proceeds in a very pure meaner and that small amount of impurities can be easily removed from the purification procedure of the subsequent deprotection reaction.

According to the present invention, the compound of formula 7 can be also prepared from direct coupling of the compound of formula 2 with 9H-4-hydroxy carbazole of formula 8. That is, the compound of formula 2 can be directly converted into the compound of 7 through coupling with the compound of formula 8, without any procedures to increase the leaving ability of the hydroxy group mediated by halogenation or sulfonation. Such a procedure is expressed as pathway (2) in the reaction scheme 4. As a result of the pathway (2), the carvedilol can be produced through reduced steps, compared to the pathway (1).

Mitsunobu reaction can be applicable to the direct coupling of the compound of formula 2 with the compound of formula 8, via the pathway (2) of the reaction scheme 4. In the mitsunobu reaction, activation of the hydroxy group of the compound 2 and in situ nucleophilic substitution are carried out as one pot reaction [*Advanced Organic Chemistry* 3rd Ed. Part B. Plenum Press, 1993; *Advanced Organic Chemistry* 4th Ed. A Wiley-Interscience Publication, 1992].

The preparation of the compound of formula 7 through the pathway (2) is explained in detail. The hetero-ring compound of formula 2 having the hydroxy group is dissolved into an organic solvent, and a mitsunobu reagent comprised of a phosphine compound of formula 11 and a dialkyl azocarboxylate of formula 12 is added to activate the hydroxy group. To the solution, 9H-4-hydroxy carbazole of formula 8 is added. Nucleophilic attack of 9H-4-hydroxy carbazole of formula 8 to the activated hydroxy group produces the compound of formula 7.

Specific examples of the compound of formula 11 and the compound of formula 12 are as follows:

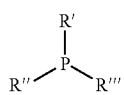

Formula 11 wherein, R', R" and R'" represent substituents. Preferably, R', R" and R'" each independently represent $C_1\sim C_6$ alkyl group, $C_3\sim C_6$ cycloalkyl group, $C_2\sim C_6$ alkenyl group, $C_2\sim C_6$ alkynyl group, $C_1\sim C_6$ alkoxy group, $C_6\sim C_{10}$ aryl group or $(CH_2)_L$—$R_3$ (wherein, $R_3$ represents $C_3\sim C_6$ cycloalkyl group, $C_2\sim C_6$ alkenyl group, $C_2\sim C_6$ alkynyl group, $C_1\sim C_6$ alkoxy group or $C_6\sim C_{10}$ aryl group and L is an integer of 1 to 8).

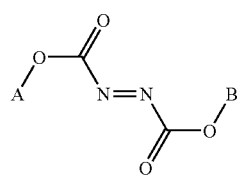

Formula 12 wherein, A and B each independently represent $C_1\sim C_6$ alkyl group, $C_3\sim C_6$ cycloalkyl group, $C_2\sim C_6$ alkenyl group or $C_2\sim C_6$ alkynyl group.

The compound of formula 7, prepared through the pathway (2) of the reaction scheme 2 can be also applicable to the subsequent deprotection reaction, without any purification procedure, because the phosphine oxide produced as a byproduct can be easily removed from the purification procedure of the following deprotection reaction. That is, the compound of formula 7 can be directly applied, without any purification, to the deprotection as one pot reaction. This provides simplicity of the process and increase of the yield.

The preparation of the carvedilol from the compound of formula 7 is illustrated in a reaction scheme 5:

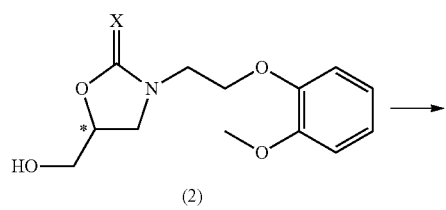

(2)

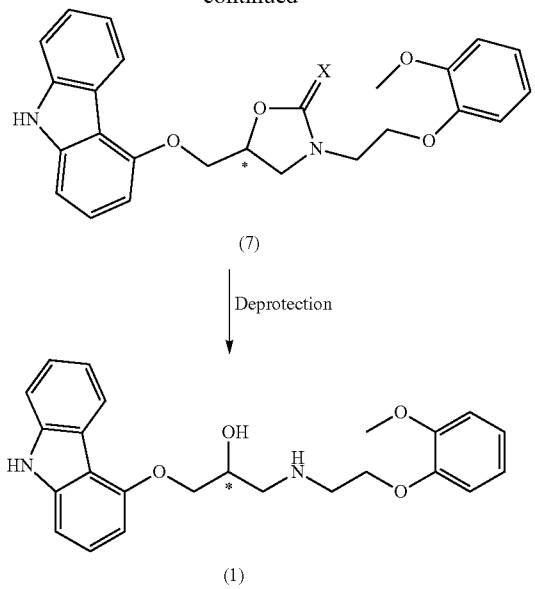

As mentioned in the above, the conversion of the compound of formula 7 to the carvedilol is accomplished by adding a base, optionally in combination with a reaction solvent, to the reactor inside which the compound of formula 7 is produced as shown in the reaction scheme 4. Generally, an oxazolidin-2-one or oxazolidin-2-thione compound undergoes a hydrolysis reaction in a basic condition, thereby producing an aminoalcohol [hydrolysis of oxazolidin-2-one: *J. Org. Chem.*, 1986, 51, 713; *J. Org. Chem.*, 1988, 53, 3865; *Tetrahedron Lett.*, 1990, 51, 7407; *Tetrahedron* 1998, 54, 7221; hydrolysis of oxazolidin-2-thione: *J. Org. Chem.*, 1992, 57, 4331; *J. Am. Chem. Soc.*, 1994, 116, 5607]. According to the present invention, the compound of formula 7 was found to be applicable to the deprotection reaction to produce the targeted carvedilol. As shown in the reaction scheme 5, after the starting material of the reaction scheme 4 has been completely consumed, a base or a combination of a base and a solvent is added to the same reactor under stirring to complete the deprotection reaction. According to preferred embodiment of the present invention, a base was added, under stirring, to the reaction mixture of the nucleophilic substitution reaction between the compound of formula 2 and the compound of formula 8, followed by addition of a solvent such as water, alcohol and a mixture thereof. Herein, the reaction temperature is typically in a range of 0~150° C., preferably 30~70° C.

The base is added, based on the compound of formula 2, in an amount of 0.8~10 equivalents, preferably 1.0~3.0 equivalents. As an inorganic base to be used, inorganic carbonate (for example, sodium carbonate, potassium carbonate, cesium carbonate or sodium bicarbonate) or inorganic hydroxide (for example, sodium hydroxide, potassium hydroxide or lithium hydroxide) can be mentioned.

As a solvent added in admixture with the base, water, alcohol or mixture thereof is generally used. Preferable example of the alcohol is $C_1\sim C_4$ alcohol such as methanol, ethanol, propanol, isopropanol, butanol, iso-butanol or t-butanol.

As mentioned in the above, the present invention is distinguished from the prior art, in that the targeted chiral carvedilol of formula 1 is effectively prepared from the chiral key intermediate of formula 2 in a highly optical purity and in a mild condition applicable to industrial mass production. Further, the chiral key intermediate is prepared, without any change of the chirality, from the optically pure chiral glycidyl derivative.

To the contrary, according to the conventional processes for the preparation of the chiral carvedilol as explained in the reaction scheme 1, the starting material, 4-(2,3-epoxypropyl) carbazole of formula 3, is not obtainable in a highly optical pure form. Specifically, the compound of formula 3 is prepared from the nucleophilic substitution reaction of chiral glycidyl m-nitrobenzenesulfonate with 9H-4-hydroxy carbazole of formula 8. Even though the reaction had been reported to proceed in a stereoselective manner such that chiral configuration of the product had been retained [*J. Org. Chem.,* 1989, 54, 1295; *Tetrahedron: Asymmetry* 1992, 3, 539], Dubois et al. reported that optical purity of the compound of formula 3 was significantly reduced in some cases [*J. Med. Chem.,* 1996, 39, 3256]. Further, according to our inventors' studies, the optical purity of the product was found to be very sensitive to the reaction condition. Therefore, the process is believed to require very strict reaction condition. As a result, the process is not applicable to industrial mass production.

According to the present invention, the key intermediate of formula 2 with a highly optical purity is prepared from the optically pure chiral glycidol derivative, without any deterioration of optical purity. Further, decrease of the optical purity does not occur in the preparation of the chiral carvedilol from the key intermediate of formula 2. Therefore, the process of the present invention provides the carvedilol in a highly optical pure form, compared to the conventional ones.

In addition, the process of the present invention does not require any extraordinary purification of the intermediate products involved in the preparation of the targeted chiral carvedilol. This implies that the process of the present invention is a very simple and economic one. Besides, the process of the present invention is carried out in a mild condition such that it neither requires vigorous reaction condition nor a strong oxidizing or reducing agent. As a result, the process of the present invention is suitable for the application to industrial mass production.

Conclusively, we established the process for the preparation of highly optical pure carvedilol from the chiral compound of formula 2, without any decrease of chirality and in an industrially applicable manner.

In the following, the present invention will be more fully illustrated referring to Examples. However, it should be understood that these Examples are suggested only for illustration and should not be construed to limit the scope of the present invention. Numerous modifications could be made without departing from the scope and the spirit of the invention.

EXAMPLES

Example 1

Preparation of (S)-3-[2-(2-methoxyphenoxy)ethyl]-5-(hydroxymethyl)oxazolidin-2-one
[Formula 2, X=oxygen]

Isobutyl-2-(2-methoxyphenoxy)ethylcarbamate 106.9 g (0.4 mol) and lithium-t-butoxide 6.40 g (0.08 mol) were dissolved into N,N-dimethylformamide (200 mL) and stirred at room temperature for 10 min. To the mixture, 69.5 g (0.44 mol) of (S)-2-oxyranylmethoxy-tetrahydropyran was added and stirred at 80° C. for 24 hours. The reaction mixture was cooled down to room temperature and was adjusted to pH 1 using 20% methyl alcohol sulfuric acid solution. The reaction mixture was further stirred at room temperature for 5 hours and neutralized using triethylamine. To the solution, water (400 mL) and dichloromethane (1000 mL) were added. After organic layer was separated from the mixture solution, it was dried with anhydrous magnesium sulfate and filtrated. Evaporation under reduced pressure gave the targeted compound of formula 2 in a liquid phase. The obtained product was subjected without any purification to the next deprotection reaction.

Yield: 104.6 g (98%)

$^1$H NMR (300 MHz, CDCl$_3$): δ 2.32 (br s, 1H), 3.65-3.74 (m, 4H), 3.80-3.92 (m, 2H), 3.85 (s, 3H), 4.18 (t, J=7.8 Hz, 2H), 4.60 (m, 1H), 6.89-6.99 (m, 4H).

Example 2

Preparation of (R)-3-[2-(2-methoxyphenoxy)ethyl]-5-(hydroxymethyl)oxazolidin-2-one
[Formula 2, X=oxygen]

Using N,N-dimethylformamide solution of isobutyl-2-(2-methoxyphenoxy)ethylcarbamate 53.46 g (0.2 mol), lithium-t-butoxide 3.20 g (0.04 mol) and (R)-2-oxyranylmethoxy-tetrahydropyran 34.76 g (0.22 mol), the procedures as described in Example 1 were carried out to obtain the targeted product.

Yield: 51.2 g (96%)

Example 3

Preparation of (S)-3-[2-(2-methoxyphenoxy)ethyl]-5-(hydroxymethyl)oxazolidin-2-one
[Formula 2, X=oxygen]

Using N,N-dimethylformamide solution of isobutyl-2-(2-methoxyphenoxy)ethylcarbamate 26.7 g (0.1 mol), lithium-t-butoxide 1.60 g (0.02 mol) and (S)-2-t-butoxymethyl-oxiran 14.3 g (0.11 mol), the procedures as described in Example 1 were carried out to obtain the targeted product.

Yield: 25.6 g (96%)

Example 4

Preparation of (R)-3-[2-(2-methoxyphenoxy)ethyl]-5-(hydroxymethyl)oxazolidin-2-one
[Formula 2, X=oxygen]

Using N,N-dimethylformamide solution of isobutyl-2-(2-methoxyphenoxy)ethylcarbamate 53.46 g (0.2 mol), lithium-t-butoxide 3.2 g (0.04 mol) and (R)-2-t-butoxymethyl-oxiran 28.6 g (0.22 mol), the procedures as described in Example 1 were carried out to obtain the targeted product.

Yield: 50.7 g (95%)

Example 5

Preparation of (S)-3-[2-(2-methoxyphenoxy)ethyl]-5-(hydroxymethyl)oxazolidin-2-thione
[Formula 2, X=sulfur]

Using N,N-dimethylformamide solution of ethyl-2-(2-methoxyphenoxy)ethylthiocarbamate 25.5 g (0.1 mol) [*J. Chem. Soc.,* 1952, 2076; *J. Chem. Soc.,* 1952, 2079; *Tetrahedron Lett.,* 1969, 3631], lithium-t-butoxide 1.6 g (0.02 mol) and (S)-2-oxyranylmethoxy-tetrahydropyran 17.38 g (0.11 mol), the procedures as described in Example 1 were carried out to obtain the targeted product.

Yield: 21.5 g (76%)

Example 6

Preparation of (R)-3-[2-(2-methoxyphenoxy)ethyl]-5-(hydroxymethyl)oxazolidin-2-thione
[Formula 2, X=sulfur]

Using N,N-dimethylformamide solution of ethyl-2-(2-methoxyphenoxy)ethylthiocarbamate 51.0 g (0.2 mol), lithium-t-butoxide 3.2 g (0.04 mol) and (R)-2-oxyranyl-methoxy-tetrahydropyran 34.76 g (0.22 mol), the procedures as described in Example 1 were carried out to obtain the targeted product.

Yield: 42.5 g (75%)

Example 7

Preparation of (S)-{3-[2-(2-methoxyphenoxy)ethyl]-2-oxooxazolidin-5-yl}methyl methanesulfonate
[Formula 10, X=oxygen, Z=methanesulfonate]

The compound of formula 2 prepared in the Example 1 53.4 g (0.2 mol) and triethylamine 30.36 g (0.3 mol) were added to dichloromethane (300 mL), and the obtained solution was cooled down to 0° C. To the solution, methanesulfonyl chloride 25.2 g (0.22 mol) was drop wisely added under stirring. The reaction solution was stirred for 3 hours and water (300 mL) was added thereto. After organic layer was separated from the mixture solution, it was dried with anhydrous magnesium sulfate and filtrated. Evaporation under reduced pressure gave the targeted compound of formula 10 in a liquid phase. The obtained product was subjected without any purification to the next procedure.

Yield: 68.4 g (99%)

Example 8

Preparation of (R)-{3-[2-(2-methoxyphenoxy)ethyl]-2-oxooxazolidin-5-yl}methyl methanesulfonate
[Formula 10, X=oxygen, Z=methanesulfonate]

Using dichloromethane solution of the compound of formula 2 prepared in Example 2 80.1 g (0.3 mol), triethylamine 45.5 g (0.45 mol) and methanesulfonyl chloride 37.8 g (0.33 mol), the procedures as described in Example 7 were carried out to obtain the targeted product.

Yield: 102.5 g (99%)

Example 9

Preparation of (S)-{3-[2-(2-methoxyphenoxy)ethyl]-2-oxothiooxazolidin-5-yl}methyl methanesulfonate
[Formula 10, X=sulfur, Z=methanesulfonate]

Using dichloromethane solution of the compound of formula 2 prepared in Example 5 28.33 g (0.1 mol), triethylamine 15.18 g (0.15 mol) and methanesulfonyl chloride 12.6 g (0.11 mol), the procedures as described in Example 7 were carried out to obtain the targeted product.

Yield: 35.7 g (99%)

Example 10

Preparation of (R)-{3-[2-(2-methoxyphenoxy)ethyl]-2-oxothiooxazolidin-5-yl}methyl methanesulfonate
[Formula 10. X=sulfur, Z=methanesulfonate]

Using dichloromethane solution of the compound of formula 2 prepared in Example 6 42.45 g (0.15 mol), triethylamine 22.8 g (0.225 mol) and methanesulfonyl chloride 18.9 g (0.165 mol), the procedures as described in Example 7 were carried out to obtain the targeted product.

Yield: 53.67 g (99%)

Example 11

Preparation of (S)-{3-[2-(2-methoxyphenoxy)ethyl]-2-oxooxazolidin-5-yl}methyl toluenesulfonate
[Formula 710, X=oxygen, Z=toluenesulfonate]

Using dichloromethane solution of the compound of formula 2 prepared in Example 1 26.7 g (0.1 mol), triethylamine 15.18 g (0.15 mol) and p-toluenesulfonyl chloride 21.0 g (0.11 mol), the procedures as described in Example 7 were carried out to obtain the targeted product.

Yield: 38.7 g (92%)

Example 12

Preparation of (R)-{3-[2-(2-methoxyphenoxy)ethyl]-2-oxooxazolidin-5-yl}methyl toluenesulfonate
[Formula 10, X=oxygen, Z=toluenesulfonate]

Using dichloromethane solution of the compound of formula 2 prepared in Example 2 42.7 g (0.16 mol), triethylamine 24.3 g (0.24 mol) and p-toluenesulfonyl chloride 33.6 g (0.176 mol), the procedures as described in Example 7 were carried out to obtain the targeted product.

Yield: 62.6 g (93%)

Example 13

Preparation of (S)-{3-[2-(2-methoxyphenoxy)ethyl]-2-oxothiooxazolidin-5-yl}methyl toluenesulfonate
[Formula 10, X=sulfur, Z=toluenesulfonate]

Using dichloromethane solution of the compound of formula 2 prepared in Example 5 28.3 g (0.1 mol), triethylamine 15.18 g (0.15 mol) and p-toluenesulfonyl chloride 21.0 g (0.11 mol), the procedures as described in Example 7 were carried out to obtain the targeted product.

Yield: 40.64 g (93%)

Example 14

Preparation of (R)-{3-[2-(2-methoxyphenoxy)ethyl]-2-oxothiooxazolidin-5-yl}methyl toluenesulfonate
[Formula 10, X=sulfur, Z=toluenesulfonate]

Using dichloromethane solution of the compound of formula 2 prepared in Example 6 25.5 g (0.09 mol), triethylamine 13.66 g (0.135 mol) and p-toluenesulfonyl chloride 19.0 g (0.1 mol), the procedures as described in Example 7 were carried out to obtain the targeted product.

Yield: 35.4 g (90%)

Example 15

Preparation of (S)-5-chloromethyl-3-[2-(2-methoxyphenoxy)ethyl]oxazolidin-2-one [Formula 10, X=oxygen, Z=chloride]

Using dichloromethane solution of the compound of formula 2 prepared in Example 1 26.7 g (0.1 mol), triethylamine 10.1 g (0.1 mol) and thionyl chloride 35.7 g (0.3 mol), the procedures as described in Example 7 were carried out to obtain the targeted product.

Yield: 26.3 g (92%)

Example 16

Preparation of (S)-5-chloromethyl-3-[2-(2-niethoxyphenoxy)ethyl]oxazolidin-2-thione [Formula 10, X=sulfur, Z=chloride]

Using dichloromethane solution of the compound of formula 2 prepared in Example 5 28.3 g (0.1 mol), triethylamine 10.1 g (0.1 mol) and thionyl chloride 35.7 g (0.3 mol), the procedures as described in Example 7 were carried out to obtain the targeted product.

Yield: 28.0 g (93%)

Example 17

Preparation of (S)-carvedilol 51.75 g (0.15 mol) of (S)-{3-[2-(2-methoxyphenoxy)ethyl]-2-oxooxazolidin-5-yl}methyl methanesulfonate prepared in Example 7 and 27.45 g (0.15 mol) of 9H-4-hydroxy carbazole were dissolved into 450 ml, of anhydrous ethyl alcohol. To the solution, 31.10 g (0.225 mol) of potassium carbonate was added and refluxed for 16 hours under stirring. After the compound of formula 10 was completely consumed, the reaction temperature was adjusted to room temperature. To the mixture, 4N KOH aqueous solution 150 mL was added and then refluxed for 6 hours under stirring. The reaction mixture was cooled down to room temperature and the ethyl alcohol was evaporated under reduced pressure. To the residue, water (200 mL) and dichloromethane (500 mL) were added and stirred for 30 min. Organic layer was separated, dried with anhydrous magnesium sulfate and filtrated. Evaporation under reduced pressure gave solid residues. To the obtained residue, ethyl acetate 150 ml was added and stirred. Through filtration and washing, the targeted (S)-carvedilol of formula 1 was obtained.

Yield: 44.5 g (73%)

$^1$H NMR (300 MHz, CDCl$_3$): δ 1.85 (br s, 1H), 2.97 (m, 1H), 3.10 (m, 3H), 3.83 (s, 3H), 4.15 (t, J=7.7 Hz, 2H), 4.18-4.29 (m, 3H), 6.66 (d, J=8.1 Hz, 1H), 6.85-6.97 (m, 4H), 7.04 (d, J=8.1 Hz, 1H), 7.25-7.38 (m, 3H), 8.19 (br s, 1H), 8.26 (d, J=7.8 Hz, 1H).

Optical purity: >99% ee [HPLC: Chirolsil SCA(−), effluent: mixture solvent of acetonitrile:methyl alcohol=2:1 containing 0.1% triethylamine, rate of effluent=1 mL/min, UV detector: 254 nm, retention time of (S)-isomer, $t_S$=23.2 min, retention time of (R)-isomer, $t_R$=20.6 min]

Example 18

Preparation of (R)-carvedilol

Using 34.5 g (0.1 mol) of (R)-{3-[2-(2-methoxyphenoxy)ethyl]-2-oxooxazoldin-5-yl}methyl methanesulfonate prepared in Example 8, 18.3 g (0.1 mol) of 9H-4-hydroxy carbazole and 20.7 g (0.15 mol) of potassium carbonate, the procedures as described in Example 17 were carried out to obtain the targeted (R)-carvedilol.

Yield: 28.8 g (71%)

Example 19

Preparation of (S)-carvedilol

Using 36.1 g (0.1 mol) of (S)-{3-[2-(2-methoxyphenoxy)ethyl]-2-oxothiooxazolidin-5-yl}methyl methanesulfonate prepared in Example 9, 18.3 g (0.1 mol) of 9H-4-hydroxy carbazole and 20.7 g (0.15 mol) of potassium carbonate, the procedures as described in Example 17 were carried out to obtain the targeted (S)-carvedilol.

Yield: 28 g (69%)

Example 20

Preparation of (R)-carvedilol

Using 43.3 g (0.12 mol) of (R)-{3-[2-(2-methoxyphenoxy)ethyl]-2-oxothiooxazolidin-5-yl}methyl methanesulfonate prepared in Example 10, 22.0 g (0.12 mol) of 9H-4-hydroxy carbazole and 24.8 g (0.18 mol) of potassium carbonate, the procedures as described in Example 17 were carried out to obtain the targeted (R)-carvedilol.

Yield: 32.6 g (67%)

Example 21

Preparation of (S)-carvedilol

Using 42.1 g (0.1 mol) of (S)-{3-[2-(2-methoxyphenoxy)ethyl]-2-oxooxazolidin-5-yl}methyl toluenesulfonate prepared in Example 11, 18.3 g (0.1 mol) of 9H-4-hydroxy carbazole and 20.7 g (0.15 mmol) of potassium carbonate, the procedures as described in Example 17 were carried out to obtain the targeted (S)-carvedilol.

Yield: 26.4 g (65%)

Example 22

Preparation of (S)-carvedilol

Using 56.8 g (0.13 mol) 의 (S)-{3-[2-(2-methoxyphenoxy)ethyl]-2-oxothiooxazolidin-5-yl}methyl toluenesulfonate prepared in Example 13, 23.8 g (0.13 mol) of 9H-4-hydroxy carbazole and 26.9 g (0.195 mol) of potassium carbonate, the procedures as described in Example 17 were carried out to obtain the targeted (S)-carvedilol.

Yield: 32.7 g (62%)

Example 23

Preparation of (S)-carvedilol

Using 28.6 g (0.1 mol) of (S)-5-chloromethyl-3-[2-(2-methoxyphenoxy)ethyl]oxazolidin-2-one prepared in

Example 15

18.3 g (0.1 mol) of 9H-4-hydroxy carbazole, 0.17 g (0.001 mol) of potassium iodide and 20.7 g (0.15 mol) of potassium carbonate, the procedures as described in Example 17 were carried out to obtain the targeted (S)-carvedilol.

Yield: 26.8 g (66%)

Example 24

Preparation of (S)-carvedilol

Using 42.8 g (0.15 mol) of (S)-5-chloromethyl-3-[2-(2-methoxyphenoxy)ethyl]oxazolidin-2-thione prepared in Example 16, 27.45 g (0.15 mol) of 9H-4-hydroxy carbazole, 0.249 g (0.0015 mol) of potassium iodide and 31.1 g (0.225 mol) of potassium carbonate, the procedures as described in Example 17 were carried out to obtain the targeted (S)-carvedilol.

Yield: 37.8 g (62%)

Example 25

Preparation of (S)-carvedilol 26.7 g (0.1 mol) of (S)-3-[2-(2-methoxyphenoxy)ethyl]-5-(hydroxymethyl)oxazolidin-2-one was dissolved into tetrahydrofuran (100 mL), and then, triphenylphosphine (31.44 g, 0.12 mol) and diisopropyl azodicarboxylate (24.2 g, 0.12 mol) were successively added to the solution. The mixture solution was stirred for 1 hour at room temperature. To the mixture solution, tetrahydrofuran solution (50 mL) containing 18.3 g (0.1 mol) of 9H-4-hydroxy carbazole was dropwisely added and stirred for 12 hours at room temperature. After the starting material, the compound of formula 2, was completely consumed, the reaction solution was evaporated under reduced pressure. To the remaining residue, ethyl alcohol 300 mL and 4N KOH aqueous solution 100 mL were added and refluxed for 6 hours under stirring. The reaction mixture was cooled down to room temperature and the ethyl alcohol was evaporated under reduced pressure. To the residue, water (200 mL) and dichloromethane (300 mL) were added and stirred for 30 min. Organic layer was separated, dried with anhydrous magnesium sulfate and filtrated. Evaporation under reduced pressure gave solid residues. To the obtained residue, ethyl acetate 150 ml was added and stirred. Through filtration and washing, the targeted (S)-carvedilol of formula 1 was obtained.

Yield: 21.1 g (52%)

Example 26

Preparation of (R)-carvedilol

Using (S)-3-[2-(2-methoxyphenoxy)ethyl]-5-(hydroxymethyl)oxazolidin-2-thione (32 g, 0.12 mol) prepared in Example 5, triphenylphosphine (37.7 g, 0.144 mol), diisopropyl azodicarboxylate (29.0 g, 0.144 mol) and 9H-4-hydroxy carbazole (22.0 g, 0.12 mol), the procedures as described in Example 25 were carried out to obtain the targeted (R)-carvedilol.

Yield: 23.4 g (48%)

The present invention provides an efficient process for the preparation of the targeted chiral carvedilol of formula 1, starting from the compound of formula 2, which is the key intermediate for the synthesis of the chiral carvedilol, either through increasing the leaving ability of the hydroxy group, alkylation with 9H-4-hydroxy carbazole and subsequent deprotection, or through direct coupling with 9H-4-hydroxy carbazole and subsequent deprotection.

In the above process, the key intermediate of formula 2 can be easily prepared in a highly optical pure form from commercially available starting materials, which is one of the advantages of the present invention. That is, the chiral glycidol or its derivatives of formula 5 and N-protected amine compound of formula 4, which are starting materials of the key intermediate of formula 2, are commercially available or industrially produced in a simple manner. Further, the preparation of the key intermediate of formula 2 from the starting materials is carried out without any decrease of optical purity such that the key intermediate can be produced in a highly optical pure form.

Furthermore, according to the present invention, the process does not involve any procedure which reduces the optical purity, during the conversion from the key intermediate of formula 2 to the carvedilol. The process is carried out in a simple manner, in a mild condition and without any extraordinary purification, thereby providing the chiral carvedilol in an economic manner.

Therefore, the present invention established an efficient process for the preparation of the chiral carvedilol with high optical purity, using the compound of formula 2 as a key intermediate for the synthesis of the chiral carvedilol, without any change of chirality and in a manner suitable for an industrial mass production.

The invention claimed is:

1. A process for the preparation of highly optical pure chiral carvedilol, comprising a) reacting a compound of formula 2 with a halogenation agent, a sulfonation agent or a mitsunobu reagent to activate a hydroxyl group of the compound of formula 2, followed by nucleophilic substitution reaction with 9H-4-hydroxy carbazole to produce a compound of formula 7, and b) subjecting the obtained compound of formula 7 to a deprotection reaction to produce the targeted chiral carvedilol of formula 1:

Formula 1

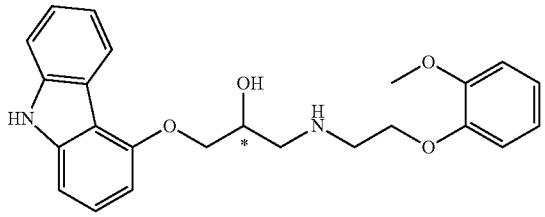

Formula 2

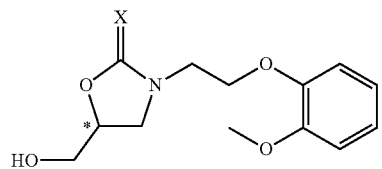

Formula 7

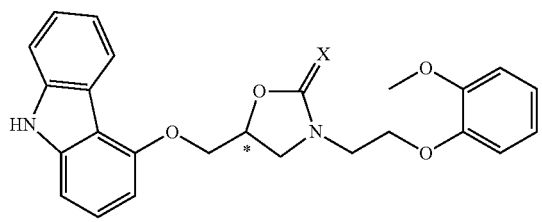

wherein, * represents a chiral center and X is oxygen or sulfur.

2. The process as set forth in claim 1, wherein the compound of formula 2 is produced by reacting an amine compound of formula 4 with a chiral glycidol compound of formula 5, followed by deprotection of a hydroxy-protecting group:

Formula 4

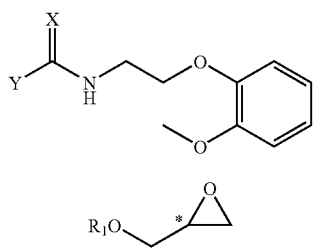

Formula 5

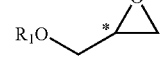

wherein, * represents a chiral center, X is oxygen or sulfur, Y is a leaving group and R₁ is a hydroxy-protecting group.

3. The process as set forth in claim 1, wherein the halogenation agent is selected from the group consisting of thionyl chloride, thionyl bromide, oxalyl chloride, phosphorous tribromide and phosphorous trichloride.

4. The process as set forth in claim 1, wherein the sulfonation agent is selected from the group consisting of methanesulfonyl chloride, p-toluenesulfonyl chloride, benzenesulfonyl chloride, trifluorornethanesulfonyl chloride and nitrobenzenesulfonyl chloride.

5. The process as set forth in claim 1, wherein the deprotection reaction of step (b) is carried out in a presence of an inorganic base.

6. A process for the preparation of highly optical pure chiral carvedilol, comprising:
reacting an amine compound of formula 4 with a chiral glycidol compound of formula 5, to produce a compound of formula 6, through ring opening of the compound of formula 5 by the compound of formula 4 and subsequent in-situ intramolecular cyclization;
deprotecting a hydroxy-protecting group of the compound of formula 6 thus obtained to produce a compound of formula 2;
reacting the compound of formula 2 with a halogenation agent, a sulfonation agent or a mitsunobu reagent to activate a hydroxyl group of the compound of formula 2, followed by nucleophilic substitution reaction with 9H-4-hydroxy carbazole to produce a compound of formula 7; and
subjecting the obtained compound of formula 7 to a deprotection reaction in a presence of an inorganic base to produce the targeted chiral carvedilol of formula 1;

Formula 1

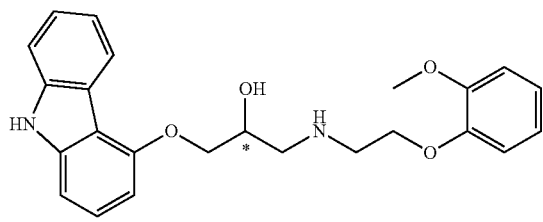

Formula 2

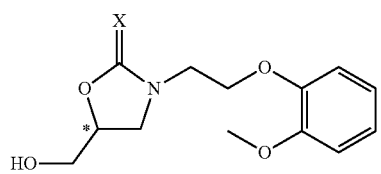

-continued

Formula 4

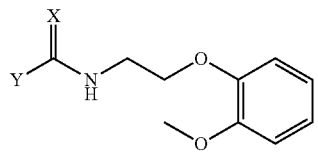

Formula 5

Formula 6

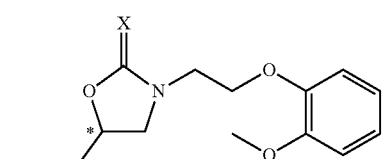

Formula 7

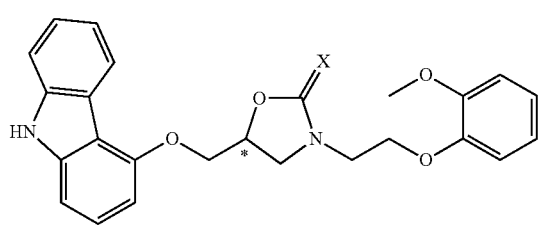

wherein, * represents a chiral center, X is oxygen or sulfur, Y is a leaving group and R₁ is a hydroxy-protecting group.

7. The process as set forth in claim 6, wherein the halogenation agent is selected from the group consisting of thionyl chloride, thionyl bromide, oxalyl chloride, phosphorous tribromide and phosphorous trichloride.

8. The process as set forth in claim 6, wherein the sulfonation agent is selected from the group consisting of methanesulfonyl chloride, p-toluenesulfonyl chloride, benzenesulfonyl chloride, trifluoromethanesulfonyl chloride and nitrobenzenesulfonyl chloride.

9. A process for the preparation of carvedilol, comprising a) reacting a compound of formula 2 with a halogenation agent, a sulfonation agent or a mitsunobu reagent to activate a hydroxyl group of the compound of formula 2, followed by nucleophilic substitution reaction with 9H-4-hydroxy carbazole to produce a compound of formula 7, and b) subjecting the obtained compound of formula 7 to a deprotection reaction to produce the carvedilol of formula 1:

Formula 1

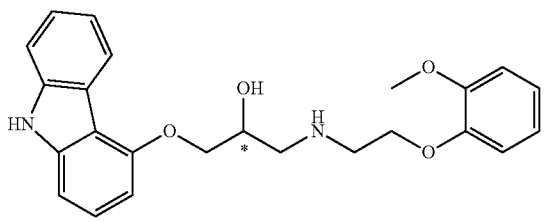

Formula 2

-continued

Formula 7

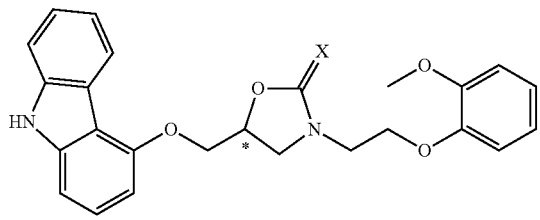

wherein, * represents a chiral center and X is oxygen or sulfur.

10. The process as set forth in claim 9, wherein the compound of formula 2 is produced by reacting an amine compound of formula 4 with a glycidol compound of formula 5, followed by deprotection of a hydroxy-protecting group:

Formula 4

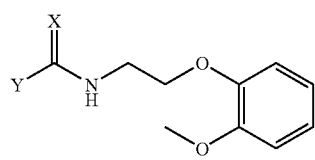

-continued

Formula 5

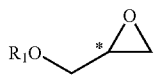

wherein, * represents a chiral center, X is oxygen or sulfur, Y is a leaving group and $R_1$ is a hydroxy-protecting group.

11. The process as set forth in claim 9, wherein the halogenation agent is selected from the group consisting of thionyl chloride, thionyl bromide, oxalyl chloride, phosphorous tribromide and phosphorous trichloride.

12. The process as set forth in claim 9, wherein the sulfonation agent is selected from the group consisting of methanesulfonyl chloride, p-toluenesulfonyl chloride, benzenesulfonyl chloride, trifluoromethanesulfonyl chloride and nitrobenzenesulfonyl chloride.

13. The process as set forth in claim 9, wherein the deprotection reaction of step (b) is carried out in a presence of an inorganic base.

* * * * *